US009884205B2

(12) United States Patent
Spittle et al.

(10) Patent No.: US 9,884,205 B2
(45) Date of Patent: Feb. 6, 2018

(54) BRACHYTHERAPY SEED INSERTION AND FIXATION SYSTEM

(71) Applicant: C. R. Bard, Inc., Murray Hill, NJ (US)

(72) Inventors: John Spittle, Dublin, OH (US); Michael W. Drobnik, Downers Grove, IL (US); Christopher D. Drobnik, Wauconda, IL (US); Mike Krachon, Atlanta, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 203 days.

(21) Appl. No.: 14/764,809

(22) PCT Filed: Mar. 14, 2014

(86) PCT No.: PCT/US2014/029331
§ 371 (c)(1),
(2) Date: Jul. 30, 2015

(87) PCT Pub. No.: WO2014/189604
PCT Pub. Date: Nov. 27, 2014

(65) Prior Publication Data
US 2015/0375011 A1   Dec. 31, 2015

Related U.S. Application Data

(60) Provisional application No. 61/784,717, filed on Mar. 14, 2013.

(51) Int. Cl.
*A61N 5/00* (2006.01)
*A61N 5/10* (2006.01)
(Continued)

(52) U.S. Cl.
CPC ............ *A61N 5/1007* (2013.01); *A61B 90/39* (2016.02); *A61M 5/3297* (2013.01);
(Continued)

(58) Field of Classification Search
CPC .......... A61N 5/00; A61N 5/10; A61N 5/1001; A61N 5/1002; A61N 5/1007; A61N 5/1008
(Continued)

(56) References Cited

U.S. PATENT DOCUMENTS 5,713,828 A * 2/1998 Coniglione ........ A61K 51/1282
600/7
6,932,758 B1 8/2005 McKenzie
(Continued)

FOREIGN PATENT DOCUMENTS

CN      2788832 Y     6/2006
CN      2803424 Y     8/2006
(Continued)

OTHER PUBLICATIONS

PCT/US14/29331 filed Mar. 14, 2014 International Search Report and Written Opinion dated Jan. 21, 2015.
(Continued)

*Primary Examiner* — John Lacyk
(74) *Attorney, Agent, or Firm* — Rutan & Tucker, LLP

(57) ABSTRACT

Brachytherapy seed insertion and fixation devices and systems to decrease implanted brachytherapy seed migration within tissue and minimize trauma. Component(s) with cavity or opening features are attached to a brachytherapy seed or series of seeds. The cavity or opening features interact with the patient's tissue to fix the seed and component assembly in place and inhibit movement/migration of the seed(s). The cavity or opening features may optionally be filled with an adhesive or other beneficial material. The seed(s) or seed and component assembly may be inserted using a delivery device having a needle through which the seed(s) or assembly are implanted and a stylet extending through the needle to cut tissue and facilitate insertion of the
(Continued)

needle. The stylet has a reduced diameter cutting tip to cut a narrow hole in tissue, and a tapered region that stretches the narrow hole to accommodate insertion of the larger diameter needle.

27 Claims, 5 Drawing Sheets

(51) Int. Cl.
    *A61M 5/32*     (2006.01)
    *A61B 90/00*     (2016.01)

(52) U.S. Cl.
    CPC ............... *A61B 2090/3925* (2016.02); *A61B 2090/3954* (2016.02); *A61B 2090/3966* (2016.02); *A61N 5/1027* (2013.01); *A61N 2005/1008* (2013.01); *A61N 2005/1024* (2013.01)

(58) Field of Classification Search
    USPC .......................................................... 600/1–8
    See application file for complete search history.

(56) References Cited

U.S. PATENT DOCUMENTS

| | | | |
|---|---|---|---|
| 2004/0068157 A1* | 4/2004 | Gellman | ............... A61N 1/406 600/4 |
| 2004/0220510 A1 | 11/2004 | Koullick et al. | |
| 2004/0242953 A1 | 12/2004 | Good | |
| 2007/0167735 A1 | 7/2007 | Zhong et al. | |
| 2007/0202151 A1 | 8/2007 | Lee et al. | |
| 2010/0094074 A1 | 4/2010 | Mark et al. | |

FOREIGN PATENT DOCUMENTS

| | | |
|---|---|---|
| CN | 102125717 A | 7/2011 |
| CN | 202538154 U | 11/2012 |
| WO | 2001/008578 A1 | 2/2001 |
| WO | 2001008578 | 2/2001 |
| WO | 2014189604 A2 | 11/2014 |

OTHER PUBLICATIONS

AU 2014269085 filed Jul. 9, 2015 Office Action dated Jul. 27, 2017.
CN 201480015405.0 filed Sep. 14, 2015 Office Action dated Jan. 19, 2017.
EP 14801097.8 filed Sep. 8, 2015 Extended European Search Report dated Sep. 5, 2016.
EP 14801097.8 filed Sep. 8, 2015 Intent to Grant dated Jun. 26, 2017.
EP 14801097.8 filed Sep. 8, 2015 Partial European Search Report dated Sep. 5, 2016.
CN 201480015405.0, filed Sep. 14, 2015 Office Action dated Sep. 6, 2017.

* cited by examiner

BRACHYTHERAPY SEED INSERTION AND FIXATION SYSTEM

PRIORITY

This application is a U.S. national stage application under 35 U.S.C. § 371 of International Application No. PCT/US14/029331, filed Mar. 14, 2014, which claims the benfit of priority to U.S. Provisional Application No. 61/784,717, filed Mar. 14, 2013, which is incorporated by reference in its entirety into this application.

BACKGROUND

Victims of cancer are often treated using chemotherapy and/or radiation therapy. Chemotherapy is the treatment of cancer by using drugs that destroy cancer cells. Radiation therapy is the use of a type of energy, called ionizing radiation, to destroy cancer cells.

Brachytherapy is one type of radiation therapy used to treat cancer. Brachytherapy involves placing a small amount of radioactive material inside the body, near the cancer cells or tumor. Unlike external radiation treatment such as electron beam irradiation, brachytherapy enables a doctor to use a higher total dose of radiation to treat a small area in a shorter amount of time. Brachytherapy may be temporary or permanent. In temporary brachytherapy, radioactive material is placed near the cancer cells or tumor for a fixed period of time, and then withdrawn. In permanent brachytherapy, radioactive material in the form of "seeds" is permanently placed near the cancer cells or tumor. Although the seeds remain in the body permanently, the radiation levels of the seeds drop off over time as radioactivity of the seeds decays.

In High-Dose Rate (HDR) brachytherapy, a specific high dose of radiation is delivered to the affected area through the delivery device for a short period of time controlled by a computer. This process may be repeated several times over the course of a single day. In Low-Dose Rate (LDR) brachytherapy, a lower dose of radiation is continuously delivered to the affected area through the delivery device over the course of hours or days.

LDR Brachytherapy has been used in the treatment of numerous types of cancer, including breast, lung, head and neck, and prostate. Cancer patients in need of brachytherapy require certain treatment regimens, i.e., a discrete number of radiological seeds arranged in a defined configuration. For example, different dosing levels or numbers of seeds may be required depending on various factors, e.g., the size of the patient, the nature of the tissue in which the seeds are to be implanted, and the type of cancer being treated.

For example, prostate cancer or other cancers may be treated using Palladium-103 or Iodine-125 seeds. Depending on the prostate size and aggressiveness of the cancer, a health care provider can determine the number and positioning of the radioactive seeds needed to deliver a sufficient amount of radiation to kill the cancerous cells.

To apply seeds to the cancer cells or tumor, a hollow tube delivery device such as a needle, catheter, or applicator may first be inserted into the affected area. Seeds are then placed in the delivery device and either pushed down the device into the proper location, or the delivery device is itself drawn out leaving the seeds seated in the proper location. Alternatively, the seeds may first be placed into the delivery device prior to the insertion of the delivery device into the body. For example, in certain brachytherapy delivery systems, the requisite number of radioactive seeds are loaded into brachytherapy needles and then inserted into the prostate.

Once the tip of the needle has been placed in its proper position, the needle is withdrawn, leaving a pattern of seeds and/or spacers in place. X-rays, ultrasound, CT, or MRI scans may be among the tools used to ensure that the seeds in the strands are properly placed.

Proper seed placement and seed retention at the implantation site influence the success or failure of a brachytherapy procedure. Certain seed implantation devices and methods often provide variable seed spacing and dosimetric patterns during and after implantation. Loose seeds, especially those that are extra-capsular (located outside the capsule of the prostate), tend to migrate and/or rotate within the patient, and as a result, may not provide radiation where needed and may sometimes cause damage to other radiation-sensitive areas of the body.

Seeds can be linked together by a connector or connective material to form a series of linked seeds or a strand of seeds. The seeds in a particular series of linked seeds or a strand may be spaced apart by a predetermined interval to create a desired dosing level. By varying the spacing of seeds and the lengths of series of linked seed or strands, linked seeds or strands can be formed with different desired dosing levels. However, even linked seeds or strands of seeds can migrate and/or rotate within the body.

Upon implantation, movement or migration of brachytherapy seeds occurs most frequently along the needle track cut by the needle during insertion. The desire to have the needle (and subsequently the seed) in the exact desired position prior to seed deployment can require several attempts to reposition the needle with new needle tracks resulting from each attempt. These repeat attempts may also contribute to gland edema and the resulting adverse effects on dosimetry.

It is theorized that seeds can move in the needle track since the track itself has a larger cross section than the seed outside diameter. For example, brachytherapy seeds are commonly deployed using an 18 G needle, with an inner diameter of 0.040" and an outer diameter of 0.048". The tissue is cut to the approximate size of the needle or just slightly smaller resulting in a cross section "cut" of about 0.040" to 0.048". This cut or needle track is larger than the common brachytherapy seed having an outer diameter of 0.032" and an assembled SourceLink® train having an outer diameter of 0.038". Accordingly, this larger track size appears to allow a seed some degree of movement along the cut track The systems, assemblies, and/or devices disclosed herein aid in fixing an implanted seed in place and preventing migration and/or rotation of implanted seeds. Further, the delivery device disclosed herein reduces the degree of trauma to the patient and helps prevent migration along the needle track.

SUMMARY

Enhancements for brachytherapy seeds and seed delivery systems to make the seeds less likely to migrate within tissue are described herein. Similar enhancements may also apply to other implants or markers, e.g., non-radioactive seeds used as markers for organ localization such as gold seeds. These enhancements may also make the seeds more visible during ultrasound, magnetic resonance or CT imaging procedures.

In one embodiment, a seed and component assembly is provided in which component(s) with cavity or opening features are attached to a brachytherapy seed with an interference fit. The cavity or opening features allow tissue to push or expand at least partially into the cavity or opening features, and interact with the tissue to fix the seed and component assembly in the proper place and orientation, preventing or inhibiting movement or migration (including at least rotation, lateral, and longitudinal motion).

In one embodiment, a seed and component assembly includes a seed comprising a radioactive material, and a component at least partially surrounding the radioactive seed, the component including at least one cavity or opening extending inwardly from an outer surface of a wall of the component.

In one embodiment, a method of inhibiting migration of a brachytherapy seed after implantation, includes attaching a component to the brachytherapy seed to form a seed and component assembly, the component including at least one cavity or opening extending inwardly from an outer surface of a wall of the component, and implanting the brachytherapy seed in a tissue of a patient such that the tissue pushes at least partially into the at least one cavity or opening and thereby inhibits rotation or migration of the seed and component assembly.

In one embodiment, a water/liquid or heat activated adhesive may be coated on a brachytherapy seed, seed and component assembly, or strand of seeds to fix it in place upon implantation in tissue. Further, component cavity or opening features similar to those discussed above may be filled with water/liquid or heat activated adhesive and act as repositories for the adhesive.

In one embodiment, component cavity or opening features similar to those discussed above may be filled with various beneficial materials or combinations of materials to improve fixation within the tissue, improve visibility, medicate, or otherwise treat the patient.

In one embodiment, a delivery device and/or system is provided that beneficially reduces the degree of trauma to the patient by minimizing the size of the needle track cut in the patient's tissue. The creating of a smaller "cut" hole helps reduce gland swelling, reduce tissue trauma and nerve damage, possibly resulting in improved dosimetry, a more reproducible implant, less morbidity, etc. Such reduced swelling would be beneficial for all seed types, but perhaps make the most impact with short-lived isotopes like Palladium-103 or Cesium-131 since the variation in degree of swelling and resolution time of the swelling would occur when the seed is delivering most of its therapeutic dose.

In one embodiment, a medical device includes a tube having an inner lumen extending from a proximal end to a distal end, and a stylet sized and configured to extend through the inner lumen of the tube. The stylet may include a main body portion with a first outer diameter less than an inner lumen diameter of the tube, a distal portion distal of the main body portion having a second outer diameter less than the first outer diameter, a tapering portion between the main body portion and the distal portion smoothly transitioning from the outer diameter of the main body portion to the outer diameter of the distal portion, and a cutting trocar distal of the distal portion.

In one embodiment, a method of accessing an interior of a patient's body includes providing a medical device. The medical device provided may include a tube having an inner lumen extending from a proximal end to a distal end, and a stylet extending through the inner lumen of the tube, the stylet having a main body portion, a distal portion distal of the main body portion having an outer diameter smaller than an outer diameter of the main body portion, and a tapering portion between the main body portion and the distal portion smoothly transitioning from the outer diameter of the main body portion to the outer diameter of the distal portion, and a cutting trocar distal of the distal portion. The method may also include inserting the medical device into a desired location in the patient's body and cutting a hole in tissue of the patient's body using the cutting trocar, the hole having a size approximately the same as the outer diameter of the distal portion. The method may also include stretching the hole over the tapering portion, onto the main body portion, and over the distal end of the tube, and withdrawing the stylet proximally to remove the stylet from the tube, while leaving the tube in the tissue.

Creating a smaller-diameter cutting track within the patient may lead to less seed migration, since the tissue would more tightly hold the implanted seeds since the cut track diameter could be less than the seed diameter. For example, because the needle track is smaller and is stretched over the brachytherapy seed(s), upon retraction of the needle the tissue will contract around the brachytherapy seed(s) to squeeze or hold it more tightly; this helps to fix the brachytherapy seed(s) in place and to prevent movement along the needle track.

The devices and methods disclosed herein are suitable for treating a number of different types of cancer (including those discussed elsewhere herein), especially tissue tumors. For example, the devices and methods can be used for insertion into the prostate gland to treat prostate cancer or the breast to treat breast cancer.

BRIEF DESCRIPTION OF THE DRAWINGS

The disclosed systems and methods can be better understood with reference to the following drawings. The components in the drawings are not necessarily to scale.

Figure 1:
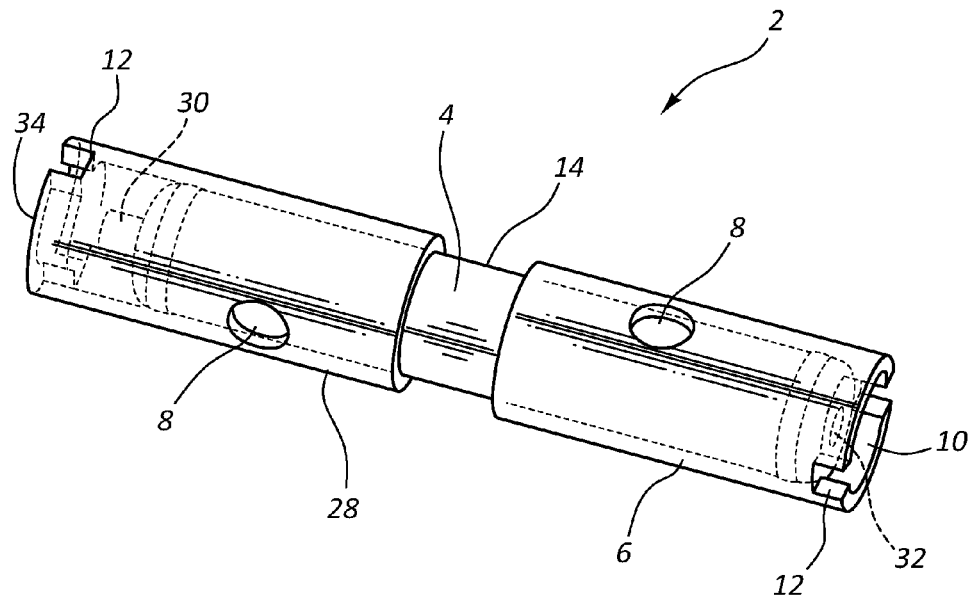
FIG. 1 shows a brachytherapy seed fixation device or assembly in the form of a seed and component assembly for use in brachytherapy treatment of a patient.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DESCRIPTION

The following description and accompanying figures, which describe and show certain embodiments, are made to demonstrate, in a non-limiting manner, several possible configurations of brachytherapy insertion and fixation devices and systems according to various aspects and features of the present disclosure.

Figure 8:
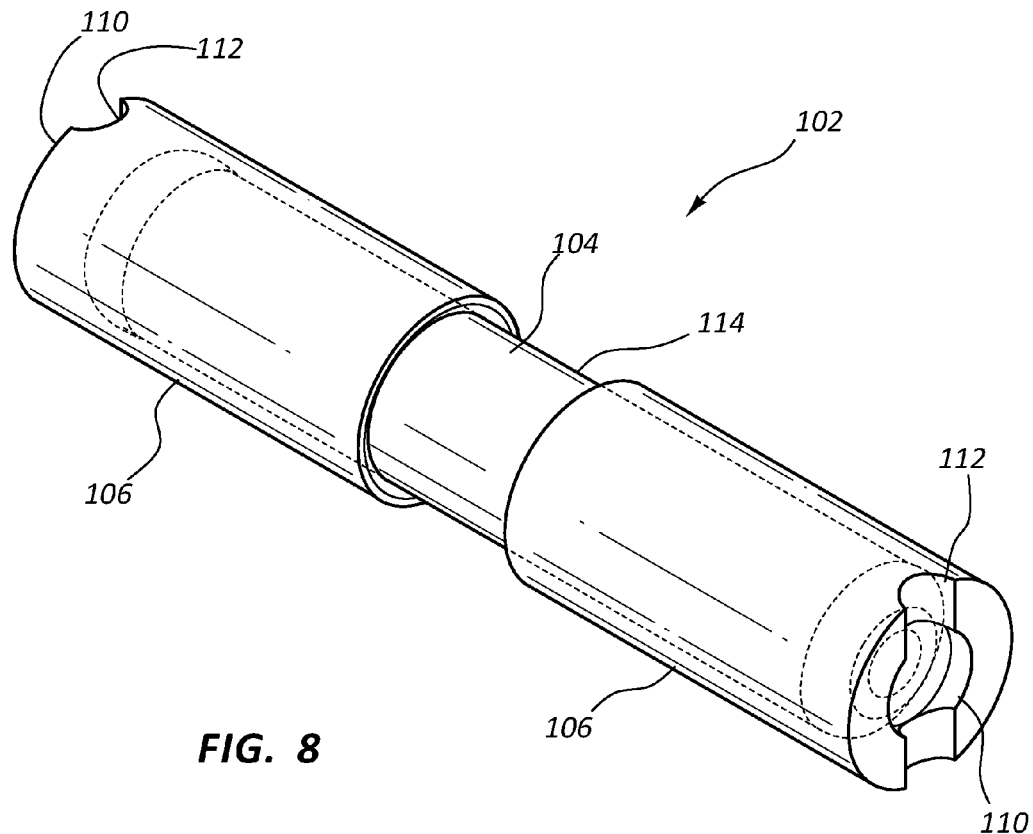
FIG. 8 shows a brachytherapy seed fixation device or assembly in the form of a seed and component assembly for use in brachytherapy treatment of a patient with two end cap components.
Figure 9:
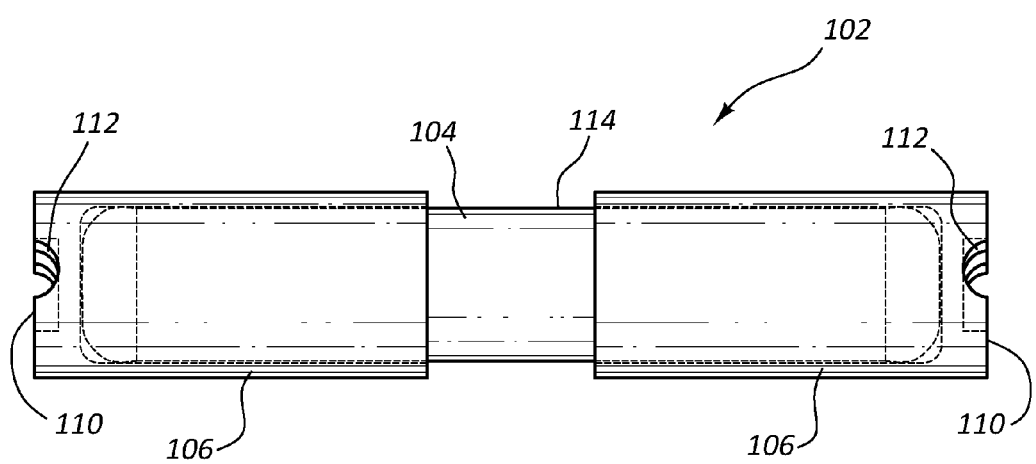
FIG. 9 shows a side view of the seed and component assembly of FIG. 8.

FIG. 1 illustrates a brachytherapy seed fixation device or assembly in the form of seed and component assembly 2 for use in brachytherapy treatment of a patient. Assembly 2 includes radioactive brachytherapy seed 4, end component 6, and intermediate connector component 28. FIGS. 8 and 9 also illustrate an embodiment of a brachytherapy seed fixation device or assembly in the form of a seed and component assembly 102 (similar to assembly 2 of FIG. 1) for use in brachytherapy treatment of a patient; however, assembly 102 includes two end components 106 in addition to radioactive brachytherapy seed 104. Components 6, 28, and 106 include cavity or opening features that are designed to "grip" within tissue to prevent motion of the seed 4. The cavity or opening features are generally in the form of a cavity, recess, or opening extending inwardly from an outer surface of the component wall. A cavity or opening feature may pass all the way through the wall of the component and be open all the way from the outer surface to the inner surface of the component wall (e.g., so the seed may be seen through the opening), or the cavity may extend partially from the outer surface toward the inner surface of the component wall.

Brachytherapy seeds 4 and 104 may include, without limit, radioactive seeds such as BrachySource® I$^{125}$ seeds and IheraSeed® Pd$^{103}$ seeds. Seeds comprising other radioactive material can be used as well, including but not limited to Cs$^{13}$, Au$^{198}$, Co$^{60}$, Ir$^{192}$, and combinations of any of the foregoing.

In FIG. 1, components 6 and 28 include cavity or opening features in the form of holes 8 in the side walls, cup 10 in the end of the component 6, notches 12 in the ends of the components 6 and 28 shaped similar to a flat head screwdriver blade—type notch, and a central band 14 in the center of the assembly where the components 6 and 28 do not cover the seed. In FIGS. 8 and 9, components 106 include similar cavity or opening features in the form of cups 110 in the end of the components 106, notches 112 in the ends of the components 106 shaped similar to a flat head screwdriver blade—type notch, and a central band 114 in the center of the assembly where the components 106 do not cover the seed; however, assembly 102 in FIGS. 8 and 9 does not include any side wall holes like holes 8. In FIG. 1, holes 8 extend radially inwardly from the outer surface to the inner surface of the wall of components 6, and leave the portion of seed 4 under holes 8 exposed. In FIGS. 1 and 8, cups 10 and 110 extend axially inwardly from the ends of components 6 and 106. Notches 12 and 112 extend both radially inwardly and axially inwardly. Central bands 14 and 114 are formed in the open space between the two components, but can be considered to extend radially inwardly from the outer surface of the walls of the two components.

Upon implantation of assembly 2 in living tissue, the tissue will push or expand at least partially into the cavity or opening features (e.g., holes 8, cups 10 and 110, notches 12 and 112, open central bands 14 and 114) in the components 6, 28, and 106. The cavity or opening features then interact with the tissue to fix the assembly (e.g., assembly 2 or 102) and seed (e.g., seed 4 or 104) in the proper place and orientation, preventing or inhibiting movement or migration (including at least rotation, lateral, and longitudinal motion).

Cavity or opening features in the components 6, 28, and 106 (e.g., the holes 8, cups 10 and 110, notches 12 and 112, open central bands 14 and 114 in FIGS. 1 and 8) are generally preferable to protrusions because cavity or opening features do not increase the diameter of the components 6, 28, or 106 and allow the assembly 2 or 102 to move smoothly down the shaft of the applicator needle. Whereas protrusions might require an increased diameter of the needle resulting in additional trauma to the patient, and might hinder the smooth progression of the seeds along the needle.

Figure 4:
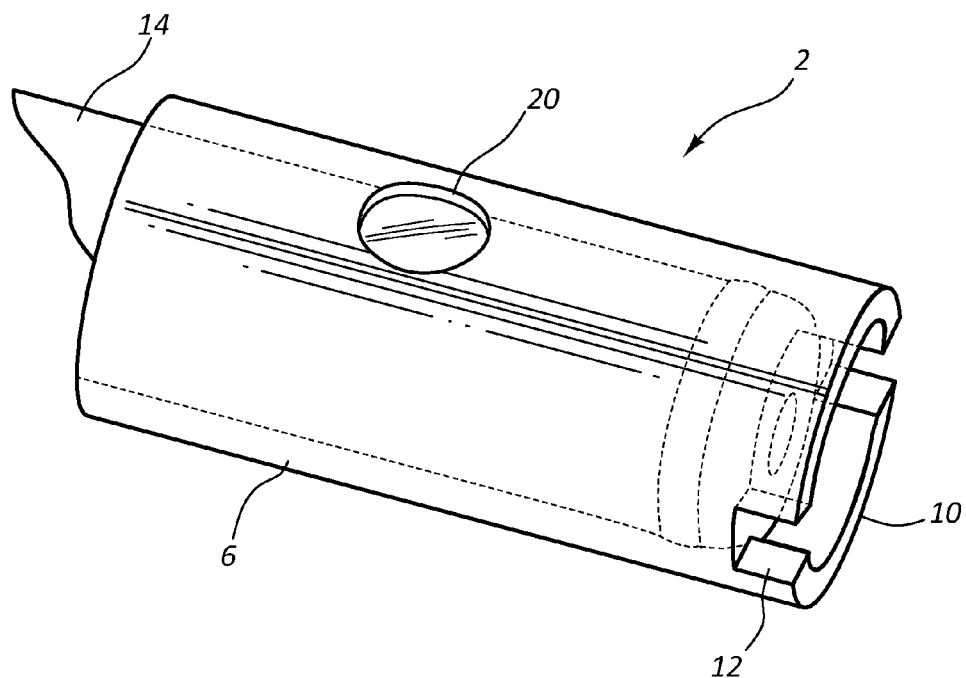
FIG. 4 shows a seed and component assembly having a cavity feature that does not extend all the way through the wall of the component (i.e., the seed is still covered by a narrow wall of the component).

Variations in the shape, size, and number of the cavity and opening features shown in FIGS. 1 and 8 may be used. For example, holes 8 and cups 10 and 110 may define a different shape, e.g., a hexagon, pentagon, rectangle, square, or triangle. However, a circular shape as used in FIG. 1 is preferred because its lack of angles allows the tissue to push into the holes 8 more evenly and resist movement equally well in any direction along the circle. Also, while FIG. 1 shows two side holes 8 in each component 6 and 28, the components 6 and 28 may include only a single side hole or additional side holes of the same or varying shapes beyond the two side holes shown. Further, while FIG. 1 shows holes 8 as passing all the way through the wall of the component and being open all the way from the outer surface to the inner surface of the component wall (e.g., so the seed may be seen through the opening), optionally, one or more of the holes or cavities may extend only partially from the outer surface toward the inner surface of the component wall (e.g., so the seed is still covered by a narrow portion of the component wall) as shown in FIG. 4 at cavity 20.

Figure 5:
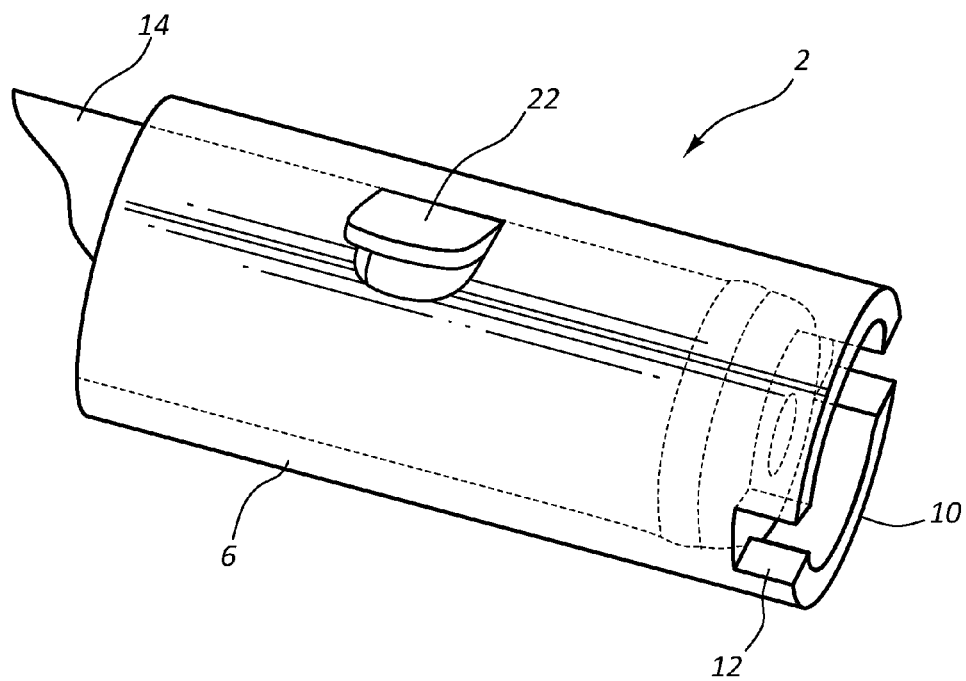
FIG. 5 shows a seed and component assembly having a flap feature to help anchor the seed and component assembly.

Alternatively, instead of holes in the walls of the end cups, "flaps" could be made by cutting U-shaped or similar patterns in the walls. These flaps may have some residual stresses and show a tendency to bow outwards, e.g., when exposed to liquid or heat, and therefore act as anchors once deployed. Such residual stresses may be imposed via an injection molding process. The flaps may be held in a collapsed position in a delivery needle or cannula, but bow or push outwardly when ejected from the delivery needle or cannula into the treatment area of the body, e.g., due to residual stresses. A combination of holes 8 and "flaps" in the same component may also be used. The flaps may be oriented in different directions, e.g., parallel, perpendicular, or oblique to the longitudinal axis of the seed. An embodiment including flap 22 is shown in FIG. 5. Further, the end cap can, optionally, have a barb or point at the end rather than a depressed area to increase fixity in tissue.

Open central bands 14 and 114 may also vary in shape. For example, the internal edges of components 6, 28, and/or 106 may be jagged, zig zag shaped, or wave (e.g., sinusoidal) shaped such that when assembled, the central band forms a non-uniform, zig zag shape, or wavy shape. This jagged, zig zag, or wavy central band is particularly beneficial because it helps to prevent rotational motion as well as longitudinal motion of the assembly 2 or 102.

Additionally, opposite facing walls forming notch 12 need not be parallel as shown in FIG. 1, but may be angled with respect to each other and/or may be curved (e.g., as shown in FIGS. 8 and 9 at notches 112). Notches 12 and 112 may also include additional slots along the perimeter of the end cap, e.g., such that notches 12 and/or 112 form a cross or Phillips screwdriver blade—like shaped notch rather than a flathead screwdriver blade—like shaped notch.

As shown in FIGS. 1 and 8, the diameter of cups 10 and 110 is somewhat less than the diameter of the seeds 4 and 104 such that the end components 6 and 106 cap the ends of seed 4 and prevent the seed from sliding out of the cup end of the components 6 and 106. Because the cups 10 shown in FIG. 1 have a smaller diameter than a brachytherapy seed and cannot connect to (or receive) a second brachytherapy seed, the components 6 and 106 are considered end caps. End cap components 6 and 106 can be placed on both ends of a brachytherapy seed as shown in FIG. 1, or only one end cap component 6 or 106 may be used on only one end of the seed. An end cap component used only on a single end of the brachytherapy seed would save money (e.g., material costs) and could be designed to act as a kind of "drag chute."

In addition to end cap components (e.g., similar to end cap components 6 and 106), intermediate connector components (e.g., similar to intermediate connector component 28) capable of connecting to a different seed at each end are also contemplated. Intermediate connector components have openings at either end large enough to receive a brachytherapy seed and may be used to link two seeds. Indeed, intermediate component 28 of FIG. 1 contains one end of seed 4 and includes an opening 34 that is sized to receive the end of a another, different brachytherapy seed. In FIG. 1, seed 4 is shown as having a receptacle or hole 32 on one end and an axial, cylindrical protrusion 30 on the other end, which allows like seeds to be connected directly to each other by inserting the protrusion 30 of one seed into the hole 32 of a second, different seed. Accordingly, two seeds may be linked by connecting protrusion 30 with hole 32 and by also linking the seeds with an intermediate connector component over the connection for added stability. However, even if the seeds do not include holes and protrusions or another means for directly connect the seeds to each other (e.g., similar to seed 104 of FIGS. 8 and 9), the seeds can still be linked by an intermediate connector component alone. A strand or series of linked seeds may be formed and customized using intermediate connector components to join a series of seeds and end cap components to cap the ends of the strand or linked seeds.

The intermediate seeds may include cavity or opening features similar to the end cap components 6 and 106 shown in FIGS. 1 and 8. For example, the intermediate connector components may include features similar to holes 8 or notches 12 and 112, and may have ends that combine with other components to form bands similar to open central bands 14 and 114. Indeed, intermediate connector component 28 of FIG. 1 includes holes 8, notches 12, and an end that combines with end component 6 to form a central band 14. Variations in these features similar to the variations discussed above with respect to the cavity and opening features of the end cap components are also possible.

It is contemplated that various combinations of the cavity or opening features shown in FIGS. 1 and 8 and discussed above may be used in various embodiments. For example, embodiments may include only one of the cavity or opening features discussed above, or may include multiple cavity or opening features of the same or different types. It is contemplated that any combination of features and/or number of features discussed above may be used in various embodiments. Also, each component in a single series of linked seeds may include the same or similar features, or each component may a different set of cavity or opening features, or some components in the series may have the same features while others are different.

The various components described herein can be made of a bioabsorbable material(s), preferably 70/30 L, D-L lactide. Other suitable bioabsorbable materials that could be used include polylactide, polyglycolic acid, polydioxanone, and polycaprolactone. A biocompatible non-bioresorbable material may also be used, e.g., a biocompatible Teflon, polyether ether ketone (PEEK), or polypropylene. The components may be manufactured by injection molding or other processes used in the art. Optionally, the mold used to make the components (e.g., injection molded components) can have a rough surface to create a mottled surface on the molded components and help to increase friction in tissue. The cavity or opening features in the components may be formed using a mold (e.g., a mold to form the components may include the inverse of the features as part of the mold), or may be cut into the sides of the formed components, e.g., using a laser cutter.

FIGS. 1 and 8 show a seed pushed into cup-like receiving portions (e.g., the larger diameter ends opposite cups 10 and 110) in the bioabsorbable components 6 and 106. However, the components could also be manufactured to be "partially formed" or have a side opening such that the seed is snapped into the component from the side. In one embodiment, two end cap components could be integrally formed together as a single component with a side opening through which one seed can be snapped into the component.

The seed and component assemblies of the various embodiments herein can be adapted to be deployed with various applicators, including Mick applicators and Mick magazines. The seeds and components of the invention can also be adapted for assembly by the end customer if desired, e.g., by using a loader similar to a SourceLink® or QuickLink® loader. This may be useful if the customer is using an intraoperative technique and uses both linked seeds and single seeds (e.g. linked seeds might be used in extracapsular positions and "capped" single seeds might be used near the urethra).

In one embodiment, structures of wires or bands can be disposed over the assembly or made part of the assembly or part of an overmolding process of the caps. These structures could lay flat during deployment so they may fit in a Mick cartridge or Mick applicator needle or other cartridge or needle, but would have portions or arms that protrude following deposition into tissue either through reaction to the body's heat or to a mechanical effect. Such structures could be made of nitinol or another suitable biocompatible material. Similarly, bimetallic strips can be incorporated as part of the assembly or structures that will "curl up" when exposed to body temperatures (e.g., like a thermostat). The resulting protrusions of these structures would anchor in tissue fixing the seed and component assembly in the proper location and orientation.

In one embodiment, a brachytherapy seed fixation device or assembly is in the form of a seed and component assembly that is coated in and/or includes repositories of water/liquid or heat activated adhesive to adhere to tissue in the body after implantation. Upon interaction with moisture in the body, water or liquid activated adhesive coated on the assembly or strand (and/or deposited in repositories) will begin to adhere to the tissue of the body and fix the assembly in place. Similarly, upon implantation of an assembly or strand coated in a heat activated adhesive, the natural body heat of the tissue will induce adhesion thereby fixing the seed and component assembly in place.

Figure 6:
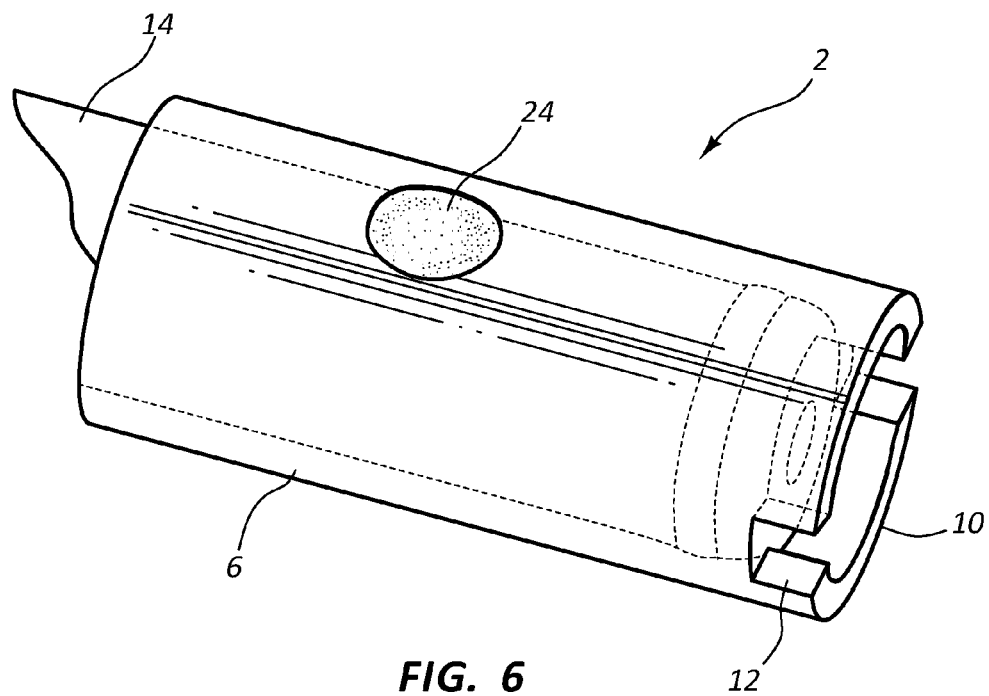
FIG. 6 shows a seed and component assembly having hole 8 filled with a beneficial material, wherein the beneficial material does not increase the diameter of the seed and component assembly.

It is contemplated that the water or heat activated glue may be used with any brachytherapy seed, seed and component assembly, or strands of seeds. However, the use of a water/liquid or heat activated adhesive is particularly effective when used in combination with a seed and component assembly including cavity or opening features similar to those discussed above and shown in FIGS. 1 and 8 above (e.g., holes 8, cups 10 and 110, notches 12 and 112, open central bands 14 and 114). The cavity or opening features of the assembly may be filled with the water/liquid or heat activated adhesive. For example, FIG. 6 shows hole 8 filled with a material 24. Material 24 is representative of any of the beneficial materials described herein as being placed within the cavity or opening features of the components, including the water/liquid or heat activated adhesive described herein. Using the cavity or opening features as repositories for the adhesive is particularly effective because it allows the use of more adhesive without a significant increase in the diameter of the seed and component assembly. Optionally, the entire assembly may be coated with adhesive in addition to filling the cavity or opening features with adhesive or, alternatively, only the cavity or opening features may be filled with adhesive while the outer surfaces of the components are not coated. Using adhesive only in the cavity or opening features is beneficial because it keeps the diameter of the assembly to a minimum and helps avoid issues with the adhesive interacting with the needle of the applicator. For example, adhesive disposed only within the repositories of the cavity or opening features is less likely to be wiped or scraped off of the assembly or strand than adhesive coated over its outer surface. Further, when the adhesive is disposed only within the repositories of the cavity or opening features it is less likely to be prematurely activated in the needle of the applicator causing sticking or otherwise interfering with the smooth passage of the assembly or strand along the needle of the applicator.

Similarly, the cavity or opening features may optionally be filled or covered with other beneficial materials (of which material 24 in FIG. 6 is representative), e.g., materials that aid in the fixation of the assembly, the visibility of the assembly using conventional imaging modalities (e.g. ultrasound, X-ray, MRI, CT), medicating a patient, or otherwise treating a patient. For example, the exposed open central band 14 may be covered with a section of tubing-shaped material (or a band/ring of material) disposed in the space between components 6 and 106. Also, holes 8, cups 10 and 110, and notches 12 and 112 can be filled with material shaped to fit in the recesses formed by these features (e.g., shaped so that they fit in the cavity or opening features, but do not increase the diameter of the assembly).

Figure 7:
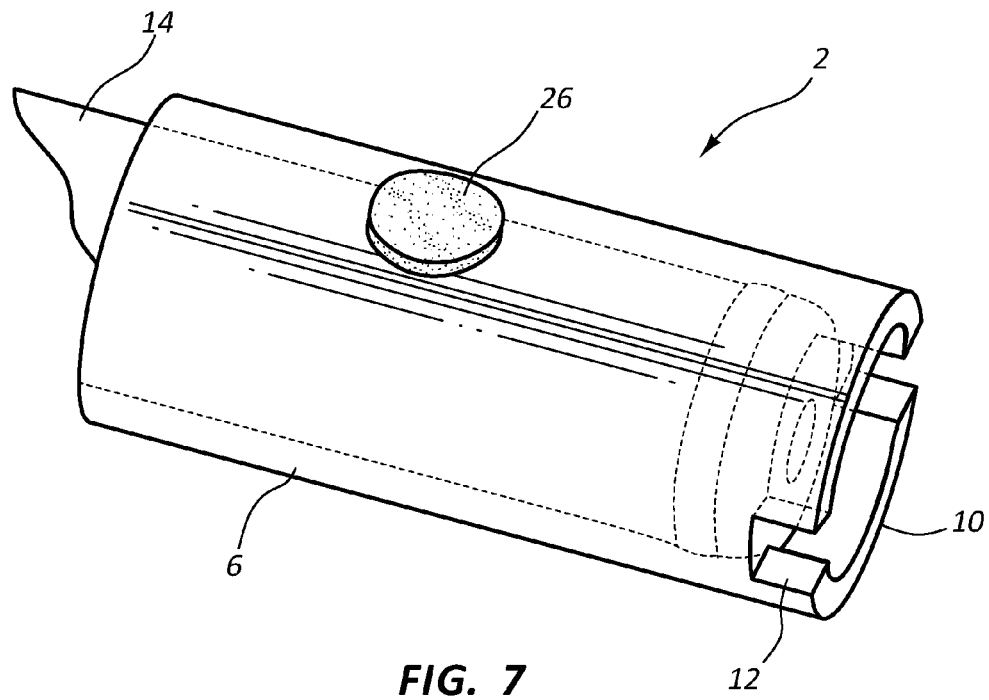
FIG. 7 shows a seed and component assembly having hole 8 filled with a swellable material that has swollen, upon exposure to liquid (e.g., body fluid) to a larger size such that the swellable material extends outside of the component to further anchor the seed and component assembly.

Beneficial materials (of which material 24 in FIG. 6 is representative) that can be included in the cavity or opening features of the various embodiments include materials that swell when exposed to liquid (like the flattened, dried sponges used when transporting vials of liquid). Preferably, the material will swell to a size at least 10% larger than its unexpanded state (or its state when initially implanted) when exposed to liquid, and more preferably at least 25% larger. When expanded, the material would extend out of the cavity or opening features and act as an anchor (e.g., a band of the material over the open central band 14 would expand to a diameter greater than the rest of the assembly after implantation and inhibit movement of the assembly). The resulting expanded material may also be more visible on ultrasound. Indeed, material may be selected that increases visibility on ultrasound or radiographically. FIG. 7 shows a swellable material 26 that, after exposure to liquid, has swelled to a larger size such that swellable material 26 extends radially outside of hole 8. Alternatively, components 6 and 106 themselves may be made of a material that swells or expands when exposed to liquid, preferably by at least 10% its unexpanded or insertion size (e.g., the walls of the components may be made at least partially of the material that swells or expands).

Alternatively, a lyophilized material, hydrogel, matrix or bioabsorbable felt can be included in the cavity or opening features (again, material 24 in FIG. 6 is representative). The lyophilized material, hydrogel, matrix or bioabsorbable felt can contain dried gadolinium, paramagnetic materials or other salts or materials that will make the seed MRI visible when dissolved in body fluids. The material could dissolve to form a film of solution around the assembly that is MRI visible. The materials or compositions described in U.S. Pat. No. 8,163,326 (which is incorporated herein) may be used in the cavity or opening features to help increase visibility of the assembly after implantation.

The material (e.g., material 24) included in the cavity or opening features could optionally be made of a fluorine containing material (e.g. Teflon) or other fluorine-containing polymer that would be visible on MRI using ultrashort echo time 19F imaging.

The material (e.g., material 24) included in the cavity or opening features may be similar to the materials discussed above but may also contain gold or gadolinium nanoparticles that would enhance the radiation dose, or may contain bioactive agents including chemotherapeutic, anti-inflammatory or analgesic agents. These agents could be contained in the material during the manufacturing process or added to the material by the end customer immediately prior to implantation.

All the cavity or opening features of a seed and component assembly may be filled with the same material or adhesive (e.g., material 24), or various combinations of materials may be used each in a different cavity or opening feature. For example, some of the cavity or opening features (e.g., holes 8) may include an adhesive, while other cavity or opening features (e.g., open central band 14) may include a material that expands when exposed to liquid. Any combination of the above materials may be used. Further, some of the cavity or opening features may include an adhesive or other material, while others features remain empty and act only as fixation features.

Figure 2:
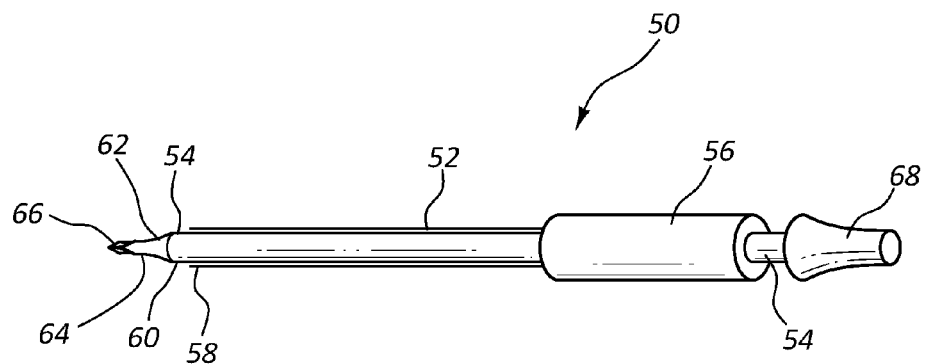
FIG. 2 shows delivery device for implanting brachytherapy seeds that helps minimize tissue trauma.
Figure 3:
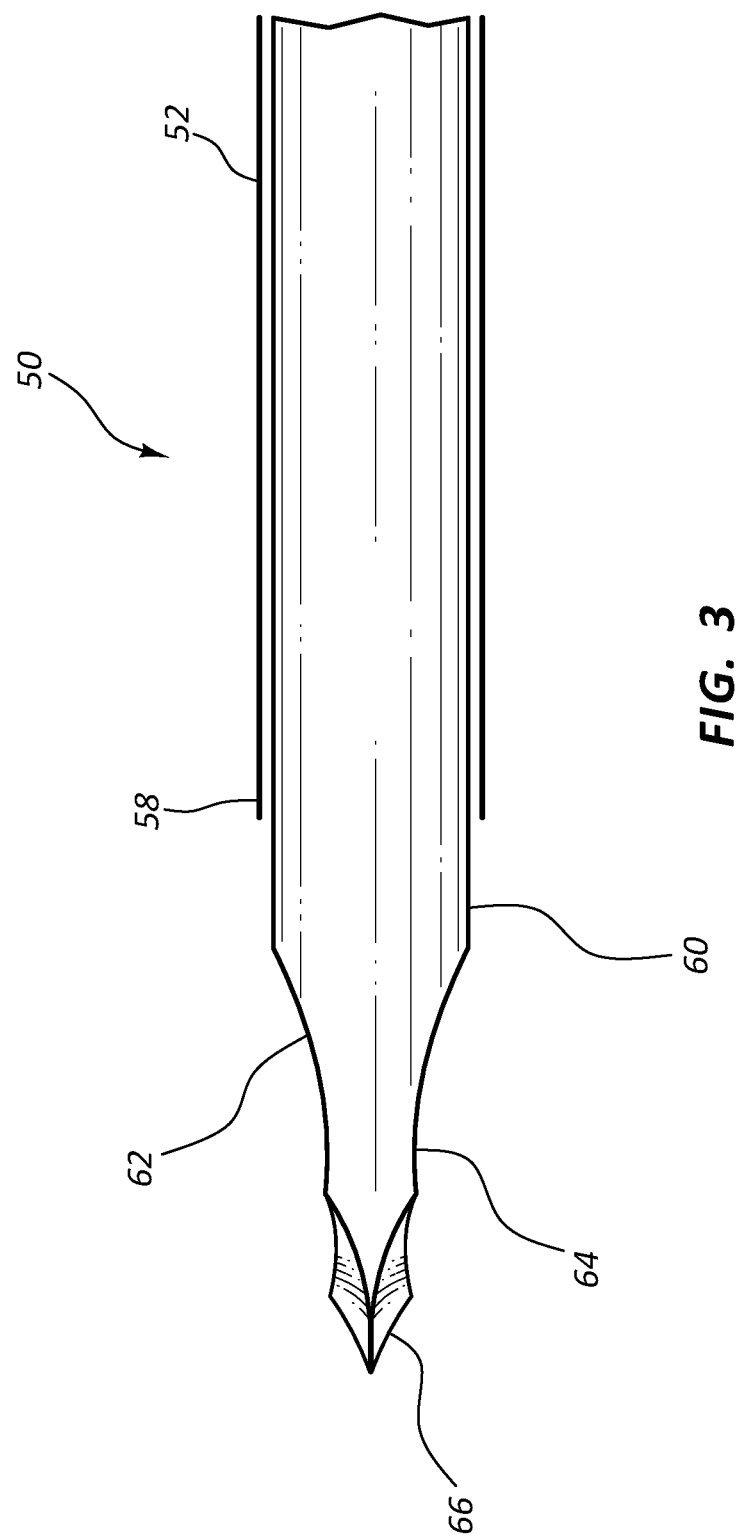
FIG. 3 shows a close up of the front portion of the delivery device of FIG. 2.

Another aspect of the invention is an improved insertion or applicator delivery device, accessory, and/or system. FIG. 2 shows an embodiment of a brachytherapy seed delivery device, accessory, or system 50. FIG. 3 shows a close up of the front portion of the delivery device/system 50. The delivery device/system 50 includes a cannula, tube, or delivery needle 52 and a stylet 54. The needle 52 is generally tubular in shape with an internal lumen through which the stylet 54 extends during insertion of the needle in tissue, and through which the treatment brachytherapy seed, seed and component assembly, and/or seed strand is ultimately implanted in the tissue of the patient. The inner lumen extends from a proximal end to a distal end of tube or needle 52. It is desired that the outer diameter of the needle be as small as possible to minimize trauma to the patient, while the inner diameter of the needle or the needle lumen be large enough to accommodate the brachytherapy seed, seed and component assembly, or seed strand to be implanted through the needle 52. While FIGS. 2 and 3 show open space between needle 52 and stylet 54 for added visibility in distinguishing the components, the needle 52 and stylet 54 can be designed to fit much more snugly together, e.g., leaving little or no open space between them. In one embodiment, the needle 52 is an 18 G needle with an inner diameter of 0.040" or 0.041" and an outer diameter of 0.048", but needle 52 can also be any other convenient size, e.g., a 17 G needle.

The needle 52 can be made of stainless steel, nitinol, plastic/polymers or other materials to give it varying degrees of stiffness, toughness, lubricity, etc. The exterior of the needle 52 or the needle tip 58 can also have some type of added lubricity (e.g. silicone) or coating (Teflon, parylene, chromium, polyurethane, etc.) and/or the needle tip 58 can be tapered to help ease the tissue from the stylet 54 onto the needle 52 as the tissue stretches and passes over the needle tip 58. The needle 52 can optionally be an outer sheath or tube made of plastic (e.g., a polyamide tube) that acts as a cannula. The size of this type of plastic outer sheath or tube may be smaller than needles of other materials, e.g., the inner diameter of this type of plastic outer sheath or tube could be about 0.034" and the outer diameter could be about 0.039". A plastic outer sheath or tube needle of this type might also be beneficial because it could be transparent allowing a clinician to see the stylet and/or seeds loaded in or extending/passing through the tube.

The stylet 54 is sized configured to extend through or traverse the inner lumen of the delivery needle 52 to cut tissue and facilitate insertion of the needle 52. A handle or gripping portion 68 is formed or attached at the proximal end of the stylet. The handle or gripping portion 68 may be used to manipulate the stylet 54 during use and to withdraw it. The main body portion or region 60 of the stylet has an outer diameter approximately the same as the inner lumen diameter of the needle 52 or only slightly less than the inner lumen diameter of the needle 52, such that the stylet can slide through the lumen of the delivery needle 52, but can also help pass the stretched tissue over the distal end of the needle 52. The stylet is "necked down" over a tapered portion or region 62 smoothly and/or gradually transitioning from the larger outer diameter main body portion/region 60 to a narrower/smaller outer diameter distal portion/region 64. The distal portion/region 64 may have a substantially uniform diameter. At the distal end of distal portion/region 64 or immediately distal of the distal portion/region 64, stylet 54 includes a cutting trocar 66. In a preferred embodiment, the distal region 64 has an outer diameter that is about half the size of the outer diameter of the main body portion/region 60. In one embodiment, stylet 54 has a 0.040" diameter main body 60 that is "necked down" over tapered region 62 to a 0.020" diameter distal portion/region 64. Cutting trocar 66 has a cutting size corresponding to the diameter of the distal portion/region 64. However, other sizes may be used.

The cutting trocar 66 shown in FIG. 3 has been ground onto the distal end of the stylet 54 in a shape similar to the tip of a Phillips head screwdriver, but with three cutting edges (i.e., looking along the longitudinal axis, the trocar 66 resembles a Mercedes star symbol). However, the cutting trocar 66 can be ground onto the tip region 64 of the stylet 54 in various configurations and shapes, e.g., the trocar may include additional cutting edges. Alternatively, the cutting trocar may be manufactured separately and attached to the distal end of the stylet.

The stylet cutting tip can be shaped like a pencil point, be necked down from the needle diameter to a smaller trocar diameter, have a shape like an arrowhead or lancet, etc. or have any other cutting tip that is typically seen with hypodermic or other needles. The stylet cutting tip, cutting trocar 66, and/or stylet 54 could also be made echogenic through surface modification, or could be made more visible by NMR, CT or fluoroscopy through the addition of materials (e.g., gold, gadolinium, or other radiopaque materials).

In use delivery device/system 50 is inserted into a desired location in the patient's body. A hole is cut in the tissue of a patient's body using the cutting trocar 66. The cutting trocar 66 on the stylet 54 is of a reduced size or diameter relative to the main body region 60 and the delivery needle 52 so that the amount of tissue cut during insertion is reduced. The narrow diameter trocar 66 cuts a small hole or narrow track in the tissue that has a size approximately the same as the size of the cutting trocar 66 (which is also approximately the size of the outer diameter of the distal portion/region 64 in a preferred embodiment). The small hole or narrow track cut in the tissue is then stretched over the "necked down" tapered region/portion 62, onto at least a portion of the main body region/portion 60, and over at least the distal end of the needle 52, such that the tissue is disposed over at least a portion of the main body 60 and the needle 52. The tissue can be stretched gradually by the tapered region 62, as the stylet 54 and needle 52 (which is disposed over the main body 60 of the stylet 54) are inserted into the tissue. In a preferred embodiment, where the outer diameter of the main body 60 is about twice as large as the outer diameter of the distal region/portion 64, the hole is stretched from a size approximately the same as the outer diameter of the distal region portion 64 to a size approximately the same as the outer diameter of the main body portion 60, and then to a size approximately the same as the outer diameter of the needle 52.

Once the tissue has been stretched around the delivery needle 52, the stylet 54 may be withdrawn proximally from the lumen of the delivery needle 52, leaving the needle 52 in place in the tissue. Accordingly, stylet 54 permits easy insertion of the delivery needle 52, even though the track or hole cut in the tissue has a smaller diameter than the delivery needle 52. Therefore, the delivery device or system 50 acts more as an "introducer" than a simple cutting instrument.

Once the needle 52 is in place in the tissue and the stylet 54 has been withdrawn, the needle 52 can be used for further treatment or diagnostics. For example, the needle 52 may act as a conduit for the introduction of a material (e.g., medication, brachytherapy seeds, diagnostic equipment) into the tissue of the body. To facilitate further treatment or diagnostics, the needle 52 may include a hub 56 formed or attached at its proximal end. The needle hub 56 can be designed and configured to mate with a another device, e.g., a Mick applicator, an endoscope, a cystoscope, another type of scope, a syringe, a delivery device, etc. Hub 56 may be Luer-shaped, funnel-shaped, or have any shape or configuration necessary to mate with another device. In other words, the hub 56 can be designed to mate with any device that might be desired to pass through or use the needle 52 for diagnostic or treatment purposes. For example, brachytherapy seeds, seed and component assemblies, and/or seed strands can be inserted through the needle 52 into the desired location in the tissue. The seeds can optionally be separated by bio-absorbable spacers. Hub 56, and needle 52 generally, can be designed to allow either manual placement of seeds down the bore (e.g., by inserting the seed, assembly, or strand through the hub 56 into the lumen and using a push rod to push it down the bore to the desired delivery site) or cartridge or machine-based delivery of seeds down the lumen (e.g., using a Mick-type applicator). Alternatively or additionally, an endoscope, cytoscope, or other type of scope may be used for further diagnostics or treatment. Also, needle 52 may be connected to a syringe or other delivery device to deliver medication through the needle 52.

The delivery device/system 50 beneficially reduces the degree of trauma to the patient by minimizing the size of the needle track cut in the patient's tissue. The creating of a smaller "cut" hole could help reduce gland swelling, reduce tissue trauma and nerve damage, possibly resulting in improved dosimetry, a more reproducible implant, less morbidity, etc. Such reduced swelling would be beneficial for all seed types, but perhaps make the most impact with short-lived isotopes like Palladium-103 or Cesium-131 since the variation in degree of swelling and resolution time of the swelling would occur when the seed is delivering most of its therapeutic dose. Delivery device/system 50 can reduce the damaged tissue area by a factor of about 4. For example, a stylet 54 with a main body diameter of 0.040" can be tapered to a stylet tip region 64 and/or cutting trocar 66 area with a diameter of 0.020", which would cut a hole or needle track of 0.020" in diameter instead of 0.040" as with unmodified stylets.

Additionally, the creating of a smaller-diameter cutting track within the patient may lead to less seed migration, since the tissue would more tightly hold the implanted seeds since the cut track diameter could be less than the seed diameter. Because the needle track is smaller and is stretched over the brachytherapy seed(s), upon retraction of the needle the tissue will contract around the brachytherapy seed(s) to squeeze or hold it more tightly; this helps to fix the brachytherapy seed(s) in place and to prevent movement along the needle track.

Optionally, the stylet 54 can be solid or can incorporate holes or channels along its length to allow dispensing of material through the stylet 54 or to equalize pressures created by withdrawing the stylet 54. For example, stylet 54 could include a channel or lumen running along the length of the stylet, e.g., a channel or lumen running through the center of the stylet 54 to an opening or openings in the distal tip region 58 of the stylet 54. The channel or lumen could be used to dispense medication (e.g., Lidocaine, anti-inflammatory medication, etc.). The opening or openings in the distal tip region 58 could be openings along the side of the stylet, and these openings could dispense medication along the needle track in the tissue. Additionally, the channel or lumen of the stylet 54 could be used to equalize pressure as the stylet 54 is withdrawn from the needle 52. Sometimes when a stylet is withdrawn from a needle implanted in tissue, a vacuum is created causing a pressure imbalance. A channel through the stylet that is open to the atmosphere at the proximal end can equalize the pressure and prevent a vacuum from forming.

In one embodiment, an insertion or applicator device uses a small-diameter flexible sheath (e.g., it could collapse to 2 dimensions or could expand like a rubber band) instead of a rigid needle or tube. A stylet similar to stylet 54 above or a stylet and cutting trocar of a uniform small diameter through its length can be used with the flexible sheath. Initially, the flexible sheath is disposed about the small diameter stylet or the small diameter stylet is passed through the flexible sheath. The stylet is then used to cut the tissue and insert the flexible sheath in the desired location in the tissue. When the stylet is removed, seeds are passed down the sheath, expanding it to the necessary outside diameter (like a snake swallowing a large rat). Further, the hole cut in the tissue by the small diameter stylet and trocar can be stretched over the seeds, seed and component assemblies, or strands of seeds as they are passed down the flexible sheath into the tissue. This embodiment helps to keep the hole cut in the tissue to a minimum.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A seed and component assembly, comprising:
   a seed comprising a radioactive material; and
   a component at least partially surrounding the seed and capping ends of the seed, the component including at least one cavity or opening feature extending radially inward from an outer surface of a wall of the component configured to allow tissue to push or expand at least partially into the at least one cavity or opening feature and to interact with the tissue to fix the seed and component assembly in a proper place and orientation, preventing or inhibiting movement or migration.

2. The assembly according to claim 1, wherein the at least one cavity or opening feature is at least two separate cavities or opening features.

3. The assembly according to claim 2, wherein each of the at least two separate cavities or opening features has a different shape.

4. The assembly according to claim 1, wherein the at least one cavity or opening feature is a hole that extends radially inward from the outer surface to an inner surface of the wall, such that a portion of the seed is exposed through the hole.

5. The assembly according to claim 1, wherein the at least one cavity or opening feature is at least partially filled with at least one of a water activated adhesive or a heat activated adhesive.

6. The assembly according to claim 1, wherein the at least one cavity or opening feature is at least partially filled with a filling material selected from the group consisting of materials that swell at least 10% when exposed to liquid, a lyophilized material, a hydrogel, a bioabsorbable felt, and a fluorine-containing polymer.

7. The assembly according to claim 6, wherein the filling material includes an added ingredient to improve visibility of the filling material after implantation selected from the group consisting of dried gadolinium, a paramagnetic material, and a salt that is Mill visible when dissolved in body fluids.

8. The assembly according to claim 1, wherein the wall of the component is at least partially formed from a material that swells at least 10% when exposed to liquid.

9. A method of inhibiting migration of a brachytherapy seed after implantation, comprising:
   attaching a component to the brachytherapy seed to partially surround the radioactive seed, cap ends of the seed, and form a seed and component assembly, the component including at least one cavity or opening feature extending radially inward from an outer surface of a wall of the component; and implanting the brachytherapy seed in a tissue of a patient such that the tissue is allowed to push or expand at least partially into the at least one cavity or opening feature to fix the seed and component assembly in a proper place and orientation, thereby inhibiting rotation or migration of the seed and component assembly.

10. A medical device, comprising:
a tube having an inner lumen extending from a proximal end to a distal end;
a stylet sized and configured to extend through the inner lumen of the tube, the stylet comprising:
  a main body portion with a first outer diameter less than an inner lumen diameter of the tube;
  a distal portion distal of the main body portion having a second outer diameter less than the first outer diameter;
  a tapering portion between the main body portion and the distal portion smoothly transitioning from the first outer diameter of the main body portion to the second outer diameter of the distal portion; and
  a cutting trocar distal of the distal portion; and
a seed and component assembly, the seed comprising a radioactive material, and the component at least partially surrounding and capping ends of the seed,
  wherein the component includes at least one cavity or opening feature extending radially inward from an outer surface of a wall of the component configured to allow tissue to push or expand at least partially into the at least one cavity or opening feature and to interact with the tissue to fix the seed and component assembly in a proper place and orientation, preventing or inhibiting movement or migration.

11. The medical device according to claim 10, wherein the first outer diameter is about twice as large as the second outer diameter.

12. The medical device according to claim 10, further comprising a hub attached to the proximal end of the tube, the hub configured to connect to a second medical device.

13. The medical device according to claim 10, wherein the tube is constructed of a transparent material, and wherein the tube is configured to accommodate the seed and component assembly upon removal of the stylet from the inner lumen of the tube.

14. The medical device according to claim 10, wherein the cutting trocar includes at least one of an echogenic surface or a radiopaque material.

15. The medical device according to claim 10, wherein the stylet includes a lumen extending from a proximal end to a distal end thereof.

16. A method of accessing an interior of a patient's body, comprising:
providing a medical device, comprising:
  a tube having an inner lumen extending from a proximal end to a distal end;
  a stylet extending through the inner lumen of the tube, the stylet having a main body portion, a distal portion distal of the main body portion having an outer diameter smaller than an outer diameter of the main body portion, a tapering portion between the main body portion and the distal portion smoothly transitioning from the outer diameter of the main body portion to the outer diameter of the distal portion, and a cutting trocar distal of the distal portion; and
  a seed and component assembly, the seed comprising a radioactive material, and the component at least partially surrounding and capping ends of the seed, the component including at least one cavity or opening feature extending radially inward from an outer surface of a wall of the component configured to allow tissue to push or expand at least partially into the cavity or opening feature and to interact with the tissue to fix the seed and component assembly in a proper place and orientation, preventing or inhibiting movement or migration of the seed and component assembly in a patient's body;
inserting the medical device into a desired location in the patient's body;
cutting a hole in tissue of the patient's body using the cutting trocar, the hole having a size approximately the same as the outer diameter of the distal portion;
stretching the hole over the tapering portion, onto the main body portion, and over the distal end of the tube; and
withdrawing the stylet proximally to remove the stylet from the tube, while leaving the tube in the tissue.

17. The method according to claim 16, further comprising inserting the seed and component assembly into the tissue through the tube after removal of the stylet.

18. The method according to claim 17, wherein the seed includes a brachytherapy seed, and inserting the seed and component assembly further comprises inserting the brachytherapy seed into the tissue through the tube.

19. The method according to claim 16, wherein the outer diameter of the main body portion is about twice as large as the outer diameter of the distal portion, and wherein stretching the hole further comprises stretching the hole from a size approximately the same as the outer diameter of the distal portion to a size approximately the same as the outer diameter of the main body portion.

20. The method according to claim 16, further comprising attaching a second medical device to a hub attached to the proximal end of the tube, the hub being configured to mate with the second medical device.

21. The assembly according to claim 1, wherein the at least one cavity or opening feature is a central band where the component does not cover the seed, the central band configured to prevent both rotational and longitudinal motion of the seed and component assembly.

22. The assembly according to claim 21, wherein internal edges of the component forming the central band are jagged, zig-zagged, or wavy to prevent the rotational and longitudinal motion of the seed and component assembly.

23. The assembly according to claim 1, further comprising cups in the component, the cups extending axially inward from ends of the component, wherein the cups are also configured to interact with the tissue to fix the seed and component assembly in the proper place and orientation, preventing or inhibiting movement or migration.

24. The assembly according to claim 22, wherein a diameter of the cups is less than a diameter of the seed to prevent the seed from sliding out of the component at either end of the component.

25. The assembly according to claim 22, further comprising notches in the ends of the component, the notches formed across the cups.

26. The assembly according to claim 1, further comprising on or more flaps formed from the wall of the component, the flaps configured to have a first, collapsed position in a tube of a medical device configured for delivering the seed and component assembly and a second, expanded position outside the tube of a medical device.

27. The assembly according to claim 1, further comprising cups in the component, the cups extending axially inward from ends of the component; and notches formed across the cups, wherein:

the cups and notches are configured to interact with the tissue to fix the seed and component assembly in the proper place and orientation, preventing or inhibiting movement or migration, and the at least one cavity or opening feature extending radially inward from the outer surface of the wall of the component includes a combination of a central band where the component does not cover the seed and holes in the wall of the component exposing the seed.

* * * * *